United States Patent [19]
Sun

[11] Patent Number: 5,962,336
[45] Date of Patent: Oct. 5, 1999

[54] MULTI-TEST PANEL

[76] Inventor: Ming Sun, V.P.R. Commerce Center, 1001 Lower Landing Rd., Blackwood, N.J. 08012

[21] Appl. No.: 08/953,930

[22] Filed: Oct. 20, 1997

[51] Int. Cl.⁶ .................................................. G01N 33/543

[52] U.S. Cl. .............................. 436/518; 422/55; 422/56; 422/58; 422/61; 435/287.1; 435/287.2; 435/287.7; 435/287.9; 435/805; 435/810; 435/970; 435/973; 435/975; 436/514; 436/169; 436/805; 436/810

[58] Field of Search .................................. 422/55–58, 61; 435/287.1, 287.2, 287.7, 287.9, 805, 810, 970, 973, 975; 436/514, 518, 169, 810, 805

[56] References Cited

U.S. PATENT DOCUMENTS

| | | | |
|---|---|---|---|
| 4,981,786 | 1/1991 | Dafforn et al. | 422/56 |
| 5,017,342 | 5/1991 | Haberzettl et al. | 436/535 |
| 5,238,652 | 8/1993 | Sun et al. | 422/61 |
| 5,260,194 | 11/1993 | Olson | 435/7.91 |
| 5,508,200 | 4/1996 | Tiffany et al. | 436/44 |
| 5,709,838 | 1/1998 | Porter et al. | 422/101 |

Primary Examiner—Christopher L. Chin
Attorney, Agent, or Firm—Norman E. Lehrer

[57] ABSTRACT

A multi-test panel with several test strips containing a separate and different immunochromatographic system, each strip being housed in a separate structure so that the structures may be joined together and interchanged, depending upon what substances within a fluid sample are being detected.

9 Claims, 3 Drawing Sheets

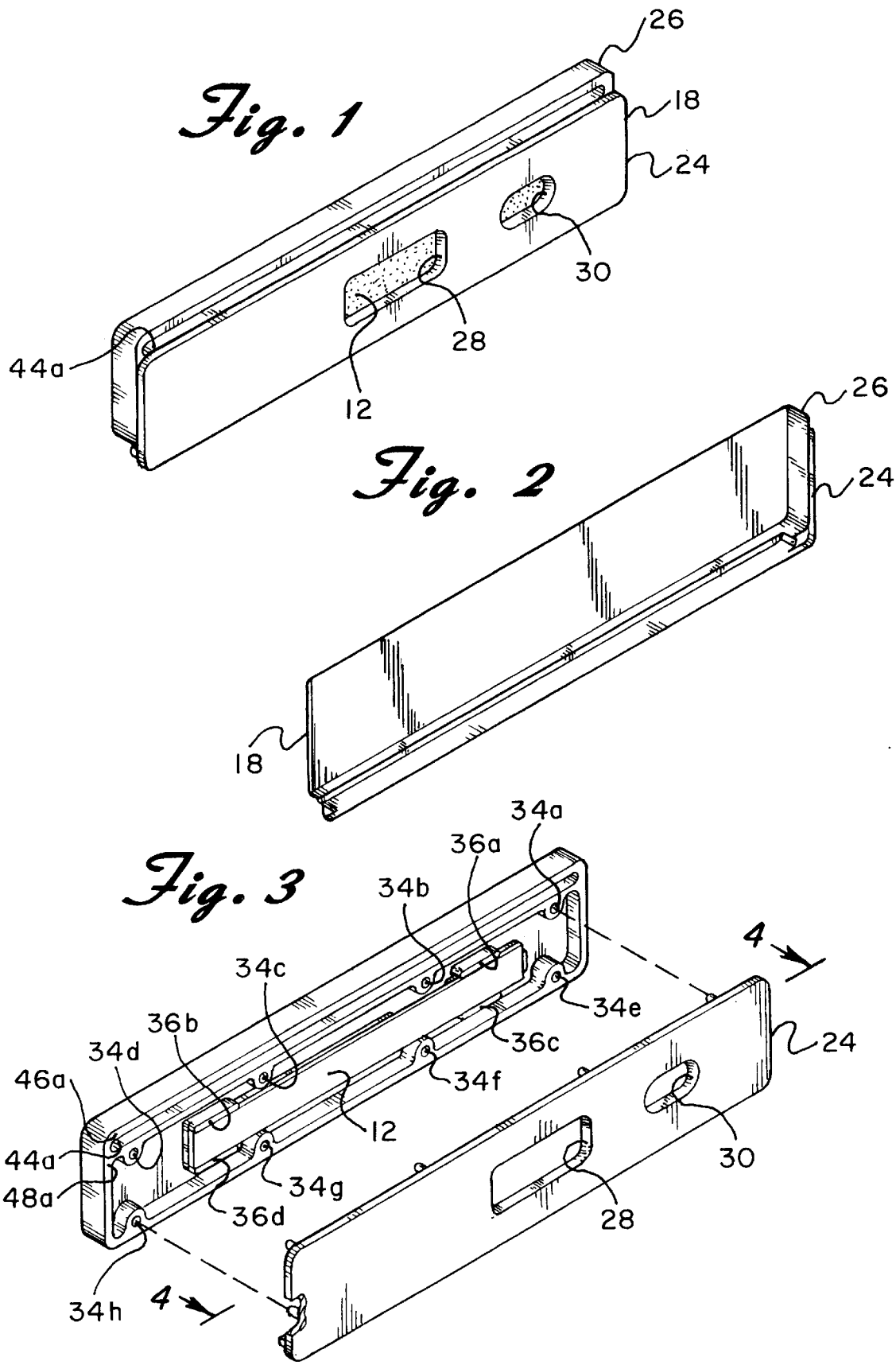

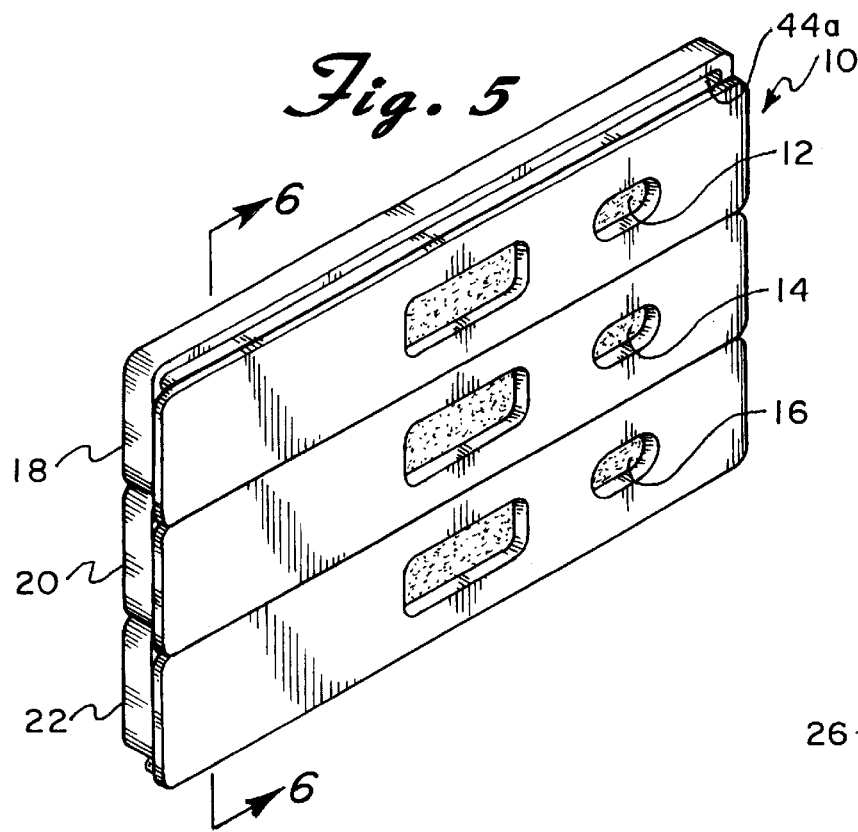
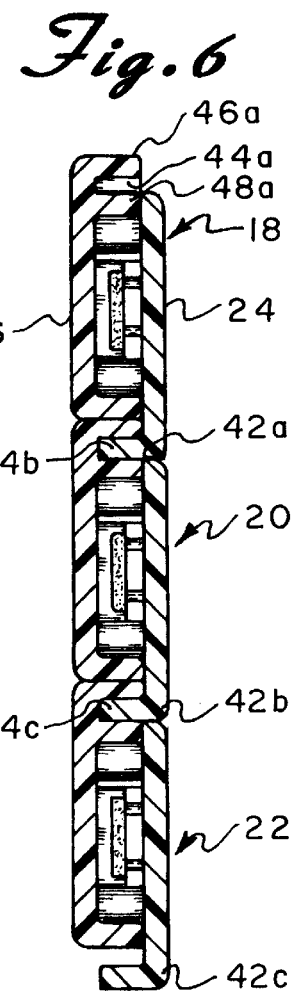
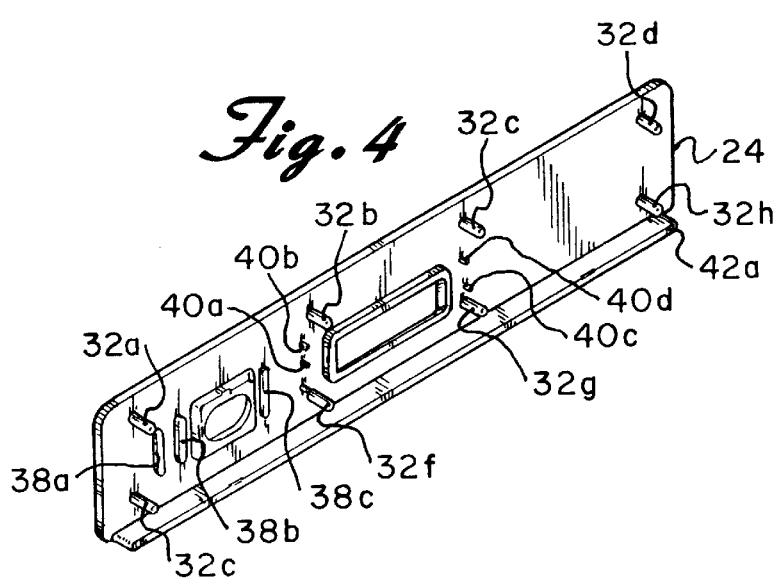

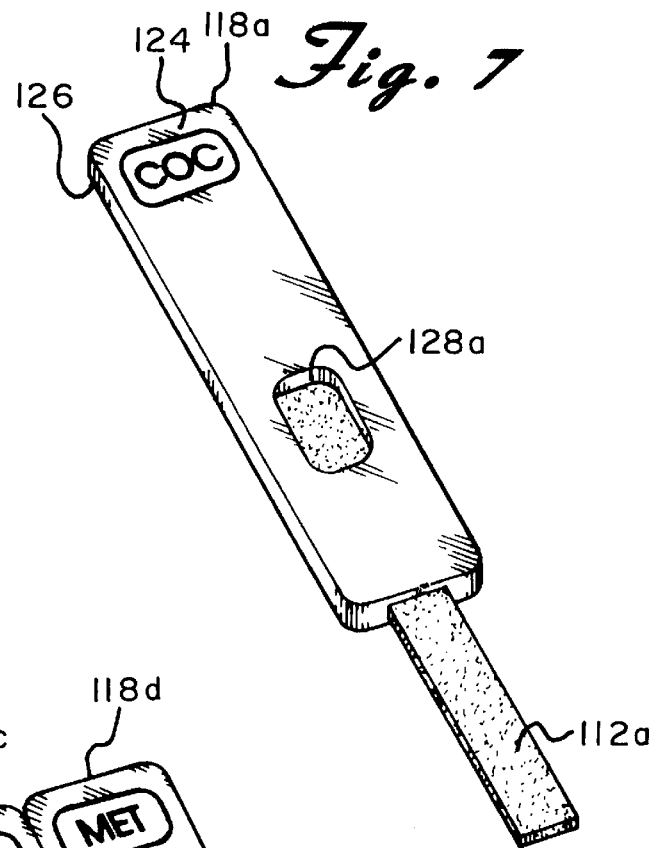
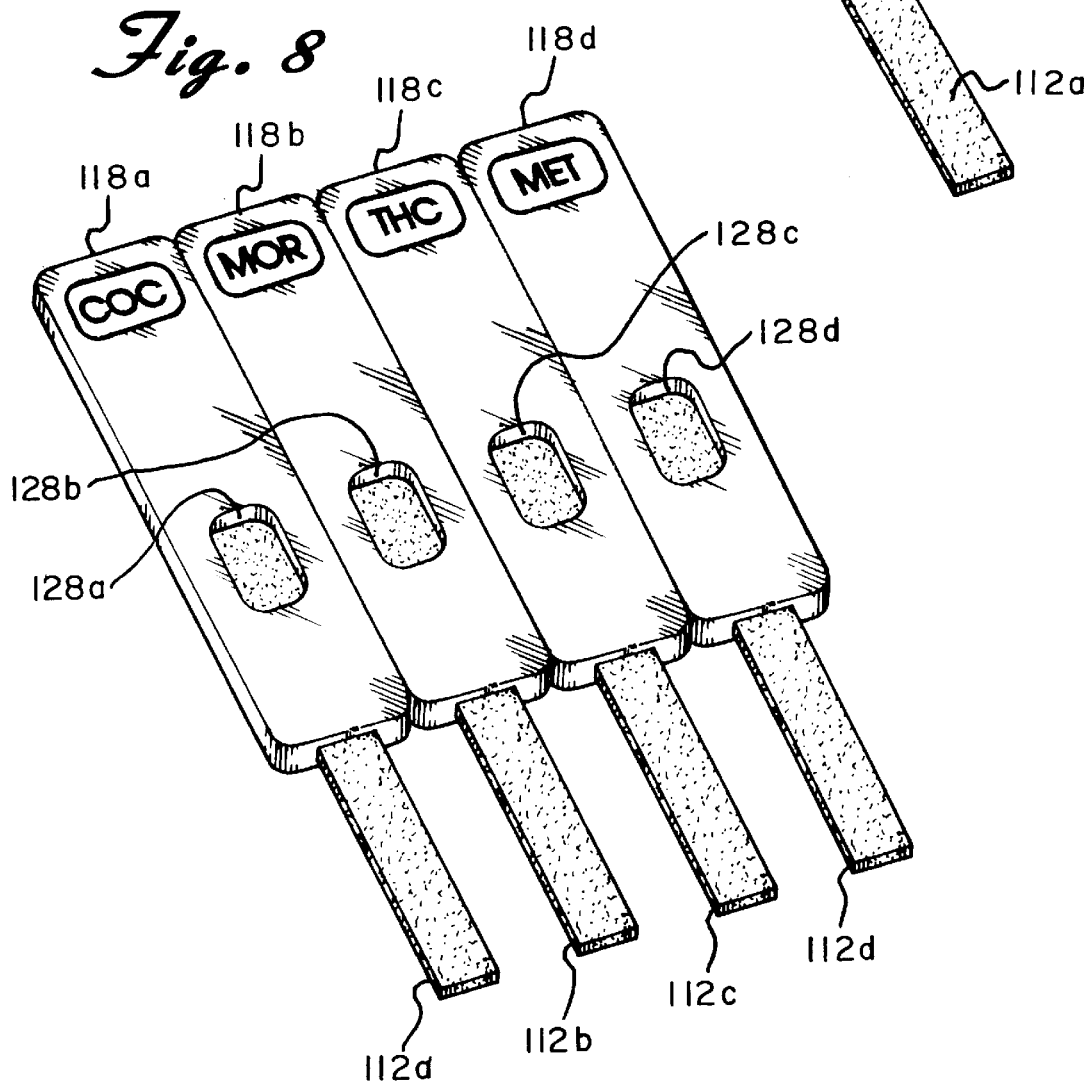

MULTI-TEST PANEL

BACKGROUND OF THE INVENTION

The present invention is directed toward an analytical test device for analyzing body fluids using immunochromotography, and more particularly toward a panel which consists of multiple tests which may be varied.

The measurement of physiologically important substances in urine, serum, and tissue using immunological principles is well known. In particular, drug-specific antibodies and antigens have been used in a variety of immunological assay procedures for detecting antibodies or antigens in bodily fluids of humans and animals. Test devices are known which can identify the presence or absence of drugs of abuse, such as cocaine, opiates, and marijuana, using the protein conjugates of these drugs and their accompanying antibodies. Multiple tests for detecting various drugs in a fluid sample where the tests are contained within a single device in a predetermined arrangement that cannot be varied are also known.

Such a multi-test device is disclosed in U.S. Pat. No. 5,260,194 to Olson which is directed toward a method and device for determining the presence of an antigen or drug which specifically binds to an antibody contained on a test strip. The strip may be a single structure such as a sheet with several lanes so that a separate and different assay may be performed in each lane. However, this device does not provide for varying the tests to be conducted so that a wide variety of tests may be performed, as needed.

U.S. Pat. No. 5,508,200 to Tiffany et al discloses a method for conducting multiple chemical assays which involves placing small volumes of samples/reagent combinations at discrete locations about a common test area on an analytical medium in order to test bodily fluids for various substances. Again, the tests contained in this device cannot be varied to suit the needs of the individual performing the test.

Also, U.S. Pat. No. 5,238,652 to Sun et al discloses an analytical test for assaying various drugs using immunochromatography. The patent discloses the use of multiple test strips in one structure but it does not disclose a structure where the test strips can be easily rearranged and varied, depending upon the needs of the individual conducting the test.

As indicated above, the problem with these multiple test devices is that the individual tests contained within the device cannot be varied. Frequently, the person conducting the test may not have a need for all of the tests contained in the device. For example, a laboratory may find that they only test for marijuana, cocaine, and heroin in the bodily fluid samples they collect. The only multi-test device available may be one that tests for marijuana, cocaine, and opium. Another, separate test would be needed to test for heroin. In this case, the multi-test device does not contain the combination of tests that the lab needs. As a result, the lab will waste the opium test every time they conduct the tests if they used the multi-test device. They must also find a separate test for heroin which may become time-consuming and expensive. If they don't use the multi-test device, they must find three individual tests, which may also become time-consuming and expensive. Furthermore, they will have at least two devices which will have to be labeled and kept together. Clearly, such a multi-test device does not fully suit the needs of the lab.

SUMMARY OF THE INVENTION

The present invention is designed to overcome the deficiencies of the prior art discussed above. It is an object of the present invention to provide a versatile multi-test panel structure which allows for testing various substances simultaneously.

Another object of the invention is to provide several test strips, each contained in separate structures where the structures may be joined to one another.

A further object of the invention is to provide a cost efficient and simple way of testing a bodily fluid sample for various drugs, disease, or pregnancy, as needed.

In accordance with the illustrative embodiments, demonstrating features and advantages of the present invention, there is provided a multi-test panel with several test strips containing a separate and different immunochromatographic system, each strip being housed in a separate structure so that the structures may be joined together and interchanged, depending upon what substances are being detected in a bodily fluid sample.

Other objects, features, and advantages of the invention will be readily apparent from the following detailed description of preferred embodiments thereof taken in conjunction with the drawings.

BRIEF DESCRIPTION OF THE DRAWINGS

For the purpose of illustrating the invention, there is shown in the accompanying drawings forms which are presently preferred; it being understood that the invention is not intended to be limited to the precise arrangements and instrumentalities shown.

FIG. 1 is a front perspective view of a first embodiment of a test strip in one of the housings of the panel of the present invention;

FIG. 2 is a rear perspective view of one of the housings of the panel of the first embodiment;

FIG. 3 is an exploded view of one of the housings and test strips of the panel of the first embodiment;

FIG. 4 is a perspective view of the inside of the top half of the housing viewed in the direction of the line 4—4 of FIG. 3;

FIG. 5 is a front perspective view of the multi-test panel of the present invention;

FIG. 6 is a cross-sectional view of the multi-test panel of the invention taken through line 6—6 of FIG. 5;

FIG. 7 is a diagrammatic view illustrating a second embodiment of a dip strip within a housing, and FIG. 8 is a diagrammatic view illustrating the second embodiment of the multi-test panel of the present invention.

DETAILED DESCRIPTION OF THE PREFERRED EMBODIMENTS

Referring now to the drawings in detail wherein like reference numerals have been used throughout the various figures to designate like elements, there is shown in FIG. 5 a multi-test panel constructed in accordance with the principles of the present invention and designated generally as 10.

The multi-test panel includes two or more test strips where each strip is contained in a separate housing. FIG. 5 depicts three such test strips 12, 14, and 16 contained in housings 18, 20, and 22, respectively, where the housings are joined together to form a panel. However, such a depiction is merely illustrative and should not be considered the only form of the multi-test panel of the present invention. Rather, any number of test strips and housings may be connected together to form the multi-test panel. Furthermore, the structure of each housing is the same, only the contents of each strip varies. Each housing is an individual, self-contained test, without being connected to another housing, and could be used as such. FIGS. 1–4 illustrate one housing and will be used to further describe the structure of the housings.

As seen in FIG. 1, housing 18 has a top half 24 and a bottom half 26. Both halves 24 and 26 are elongated and generally rectangular pieces of plastic. The top half 24 has a window 28 and a sample reception well 30 formed therein so that a test strip 12 resting within the housing 18 may be seen through both the window 28 and the well 30. The plastic may be clear or opaque. A drop of the sample to be tested is placed onto the test strip 12 through the well 30 and migrates to the rest of the strip. The result of the test can then be seen through the window 28. (The actual mechanism for the test is discussed in further detail below.) Inside the housing, pins 32a–h are located along the perimeter of the inside surface of the top half 24 with each pin extending into the housing. Each pin 32a–h fits into a respective hole 34a–h formed along the perimeter of the inside surface of the bottom half 26 of the housing 18 and holds the two halves 24 and 26 together. The bottom half 26 has teeth 36a–d located along the center thereof which hold the strip 12 in place. The top half 24 also has teeth 38a–c and protrusions 40a–d in the center which help to hold the strip in place.

Each test strip contains a different immunochromatographic system so that a different test may be conducted on each strip. That is, each strip contains a different antibody at a predetermined site on the strip. A few drops of the sample are placed into the well so that the drops migrate toward the antibody via capillary action. If the sample contains the antigen which conjugates with the antibody, colored particles contained within the strip serve as a visual indicator from the specific antigen/antibody reaction. A more detailed discussion of the immunochromatographic mechanism of the present invention may be found in U.S. Pat. 5,238,652 to Sun et al which is herein incorporated by reference.

The top half of each housing 18, 20, and 22 also has a projection 42a–c, respectively, that runs along a length thereof and extends downwardly from the inside of the top half. The projection is formed along an inside edge of the top half. The bottom half of each housing 18, 20, and 22 has a groove or recess 44a–c, respectively, that runs along an inside edge of the bottom half and is formed along a length thereof. The groove 44a, for example, is defined by spaced apart walls 46a and 48a that extend upwardly from the bottom inside surface of the bottom half 26. When the top half and bottom half of a single housing are joined together, the groove of the bottom half and the projection of the top half are on opposing side edges of the housing. As shown, the projection and groove are exposed so as to be accessible from the outside of the housing.

In order to connect one housing to another housing, the projection of one of the top halves is friction fitted into the groove of the bottom half of another housing. (See FIG. 6.) The housings are then in alignment with each other and can be easily fit together or detached. When the housings are connected together, the outer surfaces of the top halves and the outer surfaces of the bottom halves are flush with each other. Thus, several housings, each containing a test strip detecting a different substance within a fluid sample, may be joined and sold together, depending upon in which tests a physician, laboratory, or individual is interested.

In a second embodiment, as illustrated diagrammatically in FIG. 7, a dip strip 112a type test strip may be used in the multi-test panel. As in the first embodiment, each housing, seen as 118a in FIG. 7, in this embodiment has a top half 124 and a bottom half 126. With the dip strip type of test strip an end of the strip extends from the housing 118a and is dipped into a sample. Also similar to the first embodiment, each dip strip contains a different antibody at a predetermined site on the strip. The sample on the strip migrates toward the antibody via capillary action. If the sample contains the antigen which conjugates with the antibody, colored particles contained within the strip serve as a visual indicator from the specific antigen/antibody reaction. The result of the test may be seen through window 128a. Alternatively, window 128a may extend the entire length of the top half 124 of the housing 118a.

Also as in the first embodiment, the individual dip strips 112a–112d of this embodiment are each contained in separate housings 118a–118d, respectively. Each housing 118a–18d also has a window 128a–128d, respectively. (See FIG. 8.) Each of the housings 118a–118d in this embodiment has a construction similar to the housings of the first embodiment and are connected to one another in the same way that the housings in the first embodiment are connected.

In this manner, the user is not confined to a set number and type of tests just because that is the only way the tests are packaged and sold. With the present invention a series of tests may be designed and custom-made for a user, depending upon the user's needs. Therefore, an unwanted test need not be included with a test that is needed, thereby saving money and preventing the waste of a test.

The multi-test panel may also be used for a single test where each strip can detect a different concentration level of a substance. Therefore, the particular concentration level of a drug in a positive sample may be determined.

The present invention may be embodied in other specific forms without departing from the spirit or essential attributes thereof. For example, although a particular structural arrangement has been described for connecting the housings of two test strips together to form a panel, it should be readily apparent that numerous other arrangements are possible. The principle requirement is, of course, that the housings be relatively easily connected to each other to preferably form a relatively flat panel. Accordingly, reference should be made to the appended claims rather than to the foregoing specification as indicating the scope of the invention.

I claim:

1. A multi-test panel for conducting more than one immunochromatographic test comprising:

at least two housings;

each of said housings having means for releasably attaching and detaching one of said housings to the other of said housings; and a test strip containing an immunochromatographic system within each of said housings wherein each of said systems detects a different substance or concentration level of a substance in a fluid sample.

2. The multi-test panel of claim 1 wherein said attaching and detaching means includes a projection extending from one portion of each of said housings and a recess extending from another portion of each of said housings.

3. The multi-test panel of claim 1 wherein each of said housings has a top half and a bottom half, each of said halves having an inside surface, an outside surface, and side edges.

4. The multi-test panel of claim 3 wherein a projection extends from a portion of said inner surface of said top half and a recess extends along a portion of said inner surface of said bottom half.

5. The multi-test panel of claim 4 wherein said recess is defined by two walls.

6. The multi-test panel of claim 4 wherein said projection is on said side edge of said top half and said recess is on said side edge of said bottom half.

7. The multi-test panel of claim 4 wherein said projection of one of said housings is friction fitted into said recess of another of said housings.

8. The multi-test panel of claim 7 wherein said outer surfaces of said top halves are flush with each other and said outer surfaces of said bottom halves are flush with each other when said housings are connected.

9. The multi-test panel of claim 7 wherein said housings are aligned with each other when said housings are connected.

\* \* \* \* \*